United States Patent [19]
Nagatomi et al.

[11] Patent Number: 5,760,187
[45] Date of Patent: Jun. 2, 1998

[54] PURIFICATION PROCESS OF A HUMAN GROWTH HORMONE

[75] Inventors: Yuji Nagatomi; Kunizo Mori; Hideki Kobayashi, all of Chiba; Nobumi Kusuhara, Tokyo, all of Japan

[73] Assignee: Mitsui Toatsu Chemicals, Inc., Tokyo, Japan

[21] Appl. No.: 802,080

[22] Filed: Feb. 19, 1997

[30] Foreign Application Priority Data

Feb. 22, 1996 [JP] Japan ..................... 8-035064

[51] Int. Cl.⁶ ..................... B01D 15/08; C07D 251/54; C12N 15/70; C12P 21/02
[52] U.S. Cl. ..................... 530/399; 435/69.4; 530/306
[58] Field of Search ..................... 530/399, 306; 435/69.4

[56] References Cited

U.S. PATENT DOCUMENTS

| | | |
|---|---|---|
| 4,332,717 | 6/1982 | Kanaoka et al. ............ 260/112 |
| 4,342,832 | 8/1982 | Goeddel et al. ............ 435/172 |
| 5,496,713 | 3/1996 | Honjo et al. ............ 435/69.4 |

FOREIGN PATENT DOCUMENTS

| | | |
|---|---|---|
| 0587427 | 3/1994 | European Pat. Off. |
| 0741189 | 11/1996 | European Pat. Off. |
| 0753307 | 1/1997 | European Pat. Off. |
| 61-93127 | 5/1986 | Japan . |
| 1-222782 | 9/1989 | Japan . |
| WO9710887 | 3/1997 | WIPO . |

*Primary Examiner*—Cecilia J. Tsang
*Assistant Examiner*—A. Lynn Touzeau
*Attorney, Agent, or Firm*—Burns, Doane, Swecker & Mathis, L.L.P.

[57] ABSTRACT

A human growth hormone can be purified by allowing a solution containing the human growth hormone to contact with a blue pigment-bonded carrier in order to selectively adsorb the human growth hormone, then eluting the human growth hormone with an eluant of high ionic strength or an eluant containing a protein denaturing agent. This method readily enables the mass production of a highly purified human growth hormone.

8 Claims, No Drawings

PURIFICATION PROCESS OF A HUMAN GROWTH HORMONE

BACKGROUND OF THE INVENTION

1. Field of the Invention

The present invention relates to a process for the purification of a human growth hormone.

2. Description of the Related Art

A growth hormone, a typical hormone secreted from the anterior lobe of the pituitary gland, promotes body growth through the production of somatomedine in the liver, or by binding the receptor of the growth hormone. Furthermore, it has been recently revealed that the growth hormone is highly involved in the metabolism of sugars and lipids, the assimilation of proteins, and the growth and differentiation of cells. There are two known types of human growth hormone which are secreted from the human pituitary gland: one having a molecular weight of about 22,000 (hereinafter referred to as 22K hGH) and the other having a molecular weight of about 20,000 (hereinafter referred to as 20K hGH). Both 22K hGH and 20K hGH are expressed by the same hGH gene, and it is known that alternative splicing of mRNA produces 20K hGH. 22K hGH is a single chain polypeptide consisting of 191 amino acid residues, and comprises 70% to 75% of the growth hormones in the human adult pituitary gland. On the other hand, 20K hGH is a single chain polypeptide consisting of 176 amino acid residues, which corresponds to those of 22K hGH except that 15 amino acid residues from the 32nd to the 46th inclusive from the N-terminal of 22K hGH are missing. The amount of 20K hGH in the pituitary gland of a human adult is small, about 5% to 10% of the total, as compared with 22K hGH.

Use of the human growth hormone is expected to expand in the future, not only as an agent for treatment of pituitary dwarfism but also as agents for treatment of chronic renal insufficiency, bone fractures and burns. Accordingly, in order to provide a stable supply for use in the medical treatment of such disorders, it will become increasingly important to develop a process for the inexpensive mass production of a pharmaceutically acceptable high-grade human growth hormone.

There are many reports on methods for the purification of human growth hormone; however, many of them are conventional methods for the purification of proteins, e.g., a combination of the precipitation method using ammonium sulfate and liquid chromatography, which utilizes the properties of proteins, such as gel filtration chromatography and ion exchange chromatography (U.S. Pat. No. 4,342,832 and Japanese Patent No. 93127/1986). Another known method is hydrophobic chromatography (U.S. Pat. No. 4,332,717). However, the abovementioned purification methods comprise many purification steps, which in all likelihood will result in extremely poor yields and high production costs; accordingly these methods will not be effective.

In contrast to the abovementioned purification methods, affinity chromatography is the only adsorption chromatography method in which purification is carried out based on biological functions or chemical structures, and the selectivity of the absorbed substance is extremely high. Accordingly, this purification method is much more effective than those with multiple steps which are less selective, and would be useful in the mass production of highly purified substances for drugs or the like. Generally, affinity chromatography is most often used for substances with known interactions, such as an enzyme and its substrate, a sugar protein and lectin, and immunoglobulin G and Protein A. However, substances to which a human growth hormone has an affinity are not known except for proteins such as a growth hormone binding protein and anti-growth hormone antibodys, and no methods for the large scale purification of human growth hormone using commercially available affinity chromatographs have been reported.

SUMMARY OF THE INVENTION

The objective of the present invention is to establish a process for the simple mass production of a human growth hormone of high purity usable for manufacturing drugs.

As a result of extensive studies to achieve the abovementioned objective, the present inventors found that blue pigment compounds have a high affinity to a human growth hormone, that a human growth hormone can be effectively purified by affinity chromatography using a carrier bonded to a blue pigment compound, and further, that a human growth hormone can be selectively eluted by adding a protein denaturant to the eluant.

Namely, the present invention provides a process for the purification of a human growth hormone, characterized in that a solution of human growth hormone is selectively adsorbed onto a blue pigment-bonded carrier and then eluted.

The present invention readily enables the mass production of a highly purified human growth hormone by using the affinity between the human growth hormone and a blue pigment-bonded carrier and a selective elution of the human growth hormone using a protein denaturing agent, to remove impurities present in a crude solution of the human growth hormone. The mass production of a highly purified human growth hormone is very important in order to provide a stable supply of human growth hormone for pharmaceutical use.

Furthermore, the use of 20K hGH, which has minor side effects, is of great significance in order to extend the use of a human growth hormone to new applications other than the treatment of dwarfism. Accordingly, the present invention, which enables the mass production of not only conventional commercially available 22K hGH, but also of 20K hGH, which has been considered to be difficult to produce, is extremely useful.

DETAILED DESCRIPTION OF THE INVENTION AND PREFERRED EMBODIMENTS

A commercially available product, Cibachron Blue 3GA (Ciba-Geigy), can generally be used as the blue pigment to be bound to a carrier for the blue pigment-bonded carrier chromatography method of the present invention. For example, a process for the production of collagenase inhibitor using this blue pigment has been disclosed in Japanese Patent Laid-open No. 222782/1989. Cibachron Blue 3GA has the following structure (formula 1):

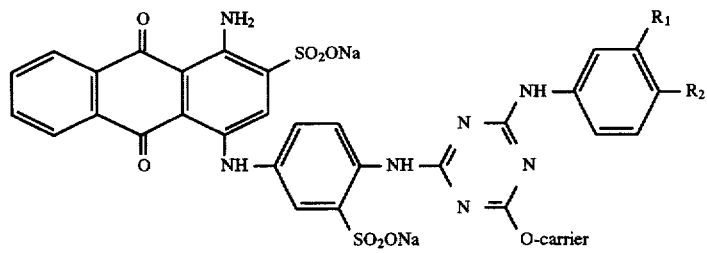

wherein $R_1$ and $R_2$ are a hydrogen atom or a —$SO_2ONa$ group.

Examples of the blue pigment-bonded carrier include Blue Sepharose CL-6B (Pharmacia), Blue Sepharose 6FF (Pharmacia), Matrex gel Blue A (Amicon), Affigel Blue (Bio-Rad Laboratories), Blue Cellulofine (Seikagaku Corp.) and TSKgel Blue-5PW (Tosoh Corp.). Furthermore, any gel which is activated and then bound to a blue pigment can also be used. Blue pigment-bonded carriers to be used in the present invention are not particularly restricted to the abovementioned carriers.

Generally, a human growth hormone can be obtained either by recombinant DNA technology or by extraction from the human pituitary gland. Either human growth hormone can be used as a starting material for the purification in a solution. Namely, the human growth hormone solution according to the present invention is an aqueous solution containing a human growth hormone which is either extracellularly secreted or intracellularly accumulated by bacterial or animal cells to which the human growth hormone gene is introduced, or a crude solution thereof, or a solution of a human growth hormone which is partially purified by a known process, such as precipitation, after homogenization of the human pituitary tissue.

The first step to carry out the present invention is to pack a column with a blue pigment-bonded carrier, wash the column with distilled water and then to equilibrate the column with a buffer solution. Examples of the buffer solution to be used include phosphate, acetate, sulfate, citrate, Tris, HEPES and borate buffer solutions. The concentration of the buffer solution is 0.005 to 0.5M, preferably 0.01 to 0.1M, more preferably 0.02 to 0.05M. The pH of the buffer solution is 5 to 8.5, preferably 6 to 7.5. The abovementioned human growth hormone solution is added onto the column thus prepared. The column is then washed with a buffer solution containing 0 to 0.3M sodium chloride or potassium chloride to remove impurities which are nonspecifically adsorbed onto the blue pigment-bonded carrier.

Elution of the human growth hormone from the blue pigment-bonded carrier column can be carried out by increasing the ionic strength of the eluant. The ionic strength of the eluant can be increased by simply increasing the concentration of the buffer solution or by adding a neutral salt such as sodium chloride and potassium chloride to the eluant. For example, the human growth hormone adsorbed onto the blue pigment-bonded carrier can be eluted by using an eluant supplemented with 1M sodium chloride.

Furthermore, the human growth hormone can be selectively eluted by using an eluant supplemented with a protein denaturant. The protein denaturant in the present invention means urea and a chaotropic reagent. Examples of the chaotropic reagent include potassium thiocyanate, sodium thiocyanate, sodium perchlorate, guanidine hydrochloride and sodium iodide.

The selective elution of the present invention is considered to be different in principle from high ionic strength elution, in the sense that it can selectively elute the human growth hormone. When urea is used as a denaturant, the concentration of urea in the eluant is 2 to 9M, preferably 4 to 6M.

In some cases, impurities may remain firmly adsorbed on the blue pigment-bonded carrier from which the human growth hormone has been eluted. In that case, the column can be regenerated by washing with a buffer solution containing 2M sodium chloride or a 0.2M aqueous sodium hydrochloride solution to remove the impurities.

The present invention will be explained by the following examples; however, the present invention is not limited to those examples.

Example 1

A crude solution for studying a method of purification of 20K hGH was prepared according to the description in U.S. Pat. No. 5,496,713. The method is briefly described as follows: Cells of an Escherichia coli transformant strain MT-10765 (deposited on Feb. 28, 1995 with Accession Number FERM BP-5020 at the National Institute of Bioscience and Human-Technology of the Agency of Industrial Science & Technology of the Ministry of International Trade and Industry according to the Budapest Treaty) were cultured in medium containing polypeptone, yeast extract, etc. After completing the culture, the bacterial cells were harvested by centrifugation, the outer membrane of the cells were burst by the osmotic shock method, the resulting fluid was centrifuged to remove cell debris, and the periplasm fraction only was recovered. The periplasm fraction was run through an anion exchange chromatography column, such as a Q Sepharose FF (Pharmacia) column, to remove nucleic acids or the like to obtain a crude 20K hGH solution.

This crude 20K hGH solution (2400 ml) was purified using Blue Sepharose 6FF (Pharmacia) as follows: 98 ml of Blue Sepharose 6FF in a column (5 cm ⌀×5 cm) were equilibrated with 300 ml of a 20 mM phosphate buffer solution (pH 6.5). The abovementioned crude 20K hGH solution was run through this column to cause the 20K hGH to adsorb onto the Blue Sepharose 6FF. The column was then thoroughly washed with a 20 mM phosphate buffer solution containing 0.3M sodium chloride (pH 6.5), after which 550 ml of a 20 mM phosphate buffer solution containing 6M urea (pH 6.5) were introduced into the column and the resulting eluate was recovered.

The amount of 20K hGH before and after purification on the Blue Sepahrose column was quantitatively measured by means of enzyme immunochemistry. The results showed that the recovery of 20K hGH by purification was as high as 96.5%. Furthermore, the specific activity, which is calculated by dividing the amount of 20K hGH by the optical density at 280 nm, was about 80 times greater after purification. Setting the optical density at 280 nm of the crude solution before application onto the column multiplied by the volume of the solution as 100%, the resulting recovery was 94.1%, 3.8% and 1.2% for the flow-through, wash and eluate, respectively. A portion of the eluate (corresponding to 5 μg of 20K hGH) was subjected to SDS polyacrylamide gel electrophoresis, after which the gel was stained with Coomassie Brilliant Blue to confirm the protein. The stain showed the presence of a single band corresponding to 20K hGH.

These results proved that 20K hGH was isolated from a crude solution containing many impurities by means of selective adsorption and separation.

Example 2

A crude solution for studying a method of purification of 22K hGH was prepared according to the description in U.S. Pat. No. 5,496,713. Namely, the 22K hGH crude solution was obtained in the same manner as briefly described in Example 1 using an Escherichia coli transformant strain MT-10773 (deposited on Feb.28, 1995 with Accession Number FERM BP-5019 at the National Institute of Bioscience and Human-Technology of the Agency of Industrial Science & Technology of the Ministry of International Trade and Industry according to the Budapest Treaty).

This crude 22K hGH solution (1200 ml) was purified using Blue Sepharose 6FF (Pharmacia) as follows: 98 ml of Blue Sepharose 6FF in a column (5 cm ⌀×5 cm) were equilibrated with 300 ml of a 20 mM phosphate buffer solution (pH 6.5). The abovementioned crude 22K hGH solution was run through this column to cause the 22K hGH to adsorb onto the Blue Sepharose 6FF. The column was then thoroughly washed with a 20 mM phosphate buffer solution containing 0.3M sodium chloride (pH 6.5), after which 550 ml of a 20 mM phosphate buffer solution containing 6M urea (pH 6.5) were introduced into the column and the eluate was recovered.

The amount of 22K hGH before and after purification on the Blue Sepahrose column was quantitatively measured by means of enzyme immunochemistry. The resulting measurements showed that the recovery of 22K hGH after purification was as high as 97.2%. Furthermore, the specific activity, which is obtained by dividing the amount of 22K hGH by the optical density at 280 nm was about 6.5 times greater after purification. Setting the optical density at 280 nm of the crude solution multiplied by the volume as 100%, the resulting recovery of each fraction was 80.9%, 4.0% and 14.9% for the flow-through, wash and eluate, respectively. A portion of the eluate (corresponding to 5 μg of 22K hGH) was subjected to SDS polyacrylamide gel electrophoresis, after which the gel was stained with Coomassie Brilliant Blue to confirm the protein. The stain showed the presence of a single band corresponding to 22K hGH.

These results proved that 22K hGH was isolated from a crude solution containing many impurities by means of selective adsorption and separation.

What is claimed is:

1. A process for the purification of a human growth hormone, wherein a human growth hormone in a solution is selectively adsorbed onto a blue pigment-bonded carrier and then eluted.

2. A process for the purification according to claim 1, wherein a human growth hormone adsorbed onto a blue pigment-bonded carrier is selectively eluted using a protein denaturing agent.

3. A method for the purification according to claim 2 wherein, wherein a human growth hormone is eluted by an eluant containing 2–9M urea.

4. A composition containing a human growth hormone obtained by the process for the purification according to claim 3.

5. A composition containing a human growth hormone obtained by the process for the purification according to claim 2.

6. A composition containing a human growth hormone obtained by the process for the purification according to claim 1.

7. The method of claim 1, wherein the blue pigment carrier has the following structure:

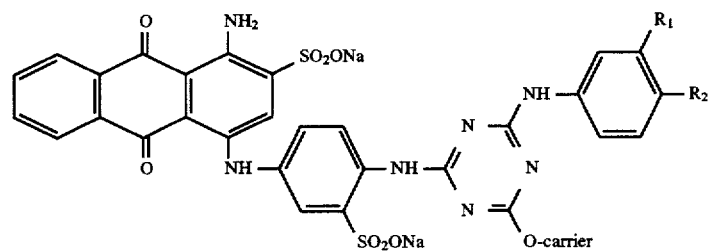
wherein $R_1$ and $R_2$ are hydrogen or a —$SO_2ONa$ group.
8. The method of claim 7, wherein the blue pigment-bonded carrier is selected from the group consisting of Blue Sepharose CL-6B, Blue Sepharose 6FF, Matrix gel Blue A, Affigel Blue, Blue Cellulofine and TSKgel Blue-5PW.
* * * * *